United States Patent [19]

Jones et al.

[11] 4,424,211

[45] Jan. 3, 1984

[54] 2'DEOXY-5-(2-HALOGENOVINYL)-URIDINES, PHARMACEUTICAL COMPOSITIONS AND METHOD OF USE

[75] Inventors: Albert S. Jones; Richard T. Walker, both of Birmingham, England; Erik D. A. de Clercq, Louvain, Belgium; Philip J. Barr, Edmonton, Canada

[73] Assignees: Rega Instituut VZW, Louvain, Belgium; University of Birmingham, Birmingham, England

[21] Appl. No.: 332,757

[22] Filed: Dec. 21, 1981

Related U.S. Application Data

[63] Continuation of Ser. No. 31,410, Apr. 19, 1979, abandoned.

[51] Int. Cl.$^3$ ..................... A61K 31/70; C07H 19/08
[52] U.S. Cl. ...................................... 424/180; 536/23; 544/309
[58] Field of Search .......................... 536/23, 180, 23; 424/180

[56] References Cited

U.S. PATENT DOCUMENTS

| | | | |
|---|---|---|---|
| 3,748,320 | 7/1973 | Vorbruggen et al. | 536/23 |
| 3,817,980 | 6/1974 | Vorbruggen et al. | 536/23 |
| 3,891,623 | 6/1975 | Vorbruggen et al. | 536/23 |
| 4,093,715 | 6/1978 | Lin et al. | 536/23 |
| 4,093,716 | 6/1978 | Lin et al. | 536/23 |
| 4,182,859 | 1/1980 | Erhardt | 536/23 |

OTHER PUBLICATIONS

Perman et al., Tetrahedron Letters 28 (1976) pp. 2427–2430.
Domin et al., Pharmacologist 17, 229 (1974).
Bobek et al., Chemistry and Biology of Nucleosides and Nucleotides (Ed Harmon, Robbins and Townsend 1978) pp. 135–148.
Baerwolff et al., Nucleic Acid Research, Spec. Publ. No. 1, (1975) pp. 529–531.
Jones et al., Tetrahedron Letters, No. 28, Jul. 1977, pp. 2459–2460.
Prusoff and Goz: Handbook of Experimental Pharmacology, Part II of Antineoplastic and Immunosuppressive Agent, (Ed Sartorelli and Johns), New York 1975.
Cheng et al., Antimicrobial Agents and Chemotherapy, 10,1, pp. 119–122.
C. C. Bhat, Synthetic Procedures in Nucleic Acid Chemistry (Ed Tipson and Zorbach), vol. 1, pp. 521–522 (1968).
Bleackley et al., Tetrahedron Letters, 32, pp. 2795–2797 (1976).
Bobek et al., J. Org. Chemistry, 40, pp. 2377–2379 (1975).
De Clercq et al., Biochemical Pharmacology, 24, pp. 532, 527 (1975).
De Clercq et al., Biochemical Pharmacology, 26, pp. 794–797 (1977).

*Primary Examiner*—Johnnie R. Brown
*Attorney, Agent, or Firm*—Birch, Stewart, Kolasch & Birch

[57] ABSTRACT

The novel substance E-5-(2-bromovinyl)-2'-deoxyuridine and its corresponding iodovinyl derivative are gifted with specific antiviral activities towards herpes simplex virus. They may be synthesized by a condensation reaction followed by separation of anomers.

9 Claims, No Drawings

2'DEOXY-5-(2-HALOGENOVINYL)-URIDINES, PHARMACEUTICAL COMPOSITIONS AND METHOD OF USE

This application is a continuation, of copending application Ser. No. 031,410, filed on Apr. 19, 1979, now abandoned.

This invention relates to 2'-deoxy-5-(2-halogenovinyl)-uridines and in particular to E-5-(2-bromovinyl)-2'-deoxyuridine and E-5-(2-iodovinyl)-2'-deoxyuridine. Further, it relates to the chemical synthesis and pharmaceutical use of such compounds and to an intermediate product which is useful in the chemical synthesis thereof.

E-5-(2-bromovinyl)-2'-deoxyuridine and E-5-(2-iodovinyl)-2'-deoxyuridine or more systematically E-5-(2-bromovinyl)- and E-5-(2-iodovinyl)-1-(2'-deoxy-β-D-erythro-pentofuranosyl)-1,2,3,4-tetrahydropyrimidin-2,4-dione, are new chemical compounds which may be represented by the following structural formula (I), wherein Hal is a bromine or iodine atom:

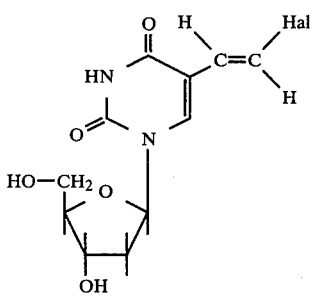

They may be prepared by condensation of a protected 2-deoxy-D-erythro-pentofuranosyl derivative with a bis(trialkyl)-silyl derivative of E-5-(2-bromovinyl)uracil or E-5-(2-iodovinyl)-uracil, followed by removal of any trialkylsilyl and hydroxyl protecting groups.

Investigations have shown that E-5-(2-bromovinyl)-2'-deoxyuridine and E-5-(2-iodovinyl)-2'-deoxyuridine are gifted with an antiviral activity which is very selective towards herpes simplex virus. Moreover, they have a remarkably low toxicity, thus resulting in a high antiviral index against this type of virus and making them very useful for the treatment of diseases caused by herpes simplex virus in man and animal.

The state of the art already includes some related deoxyuridine derivatives having antiviral activities. Thus, antiviral activities have been shown for 2'-deoxy-5-iodouridine (Prusoff and Goz: Handbook of Experimental Pharmacology, Part II of Antineoplastic and Immunosuppressive Agents. Editors: A. C. Sartorelli and D. G. Johns, Springer-Verlag, New York 1975, page 272–347) and for 2'-deoxy-5-vinyluridine (Cheng et al, Antimicrobial Agents and Chemotherapy, vol. 10, 1, 119–122 (1976)). The antiviral activities of these known compounds are not very specific, however, since they act equally well against different DNA viruses such as vaccinia and herpes simplex. Moreover, the toxicity of these compounds and especially that of 2'-deoxy-5-iodouridine, cannot be neglected. Therefore, it is surprising to see that the new compounds E-5-(2-bromovinyl)-2'-deoxyuridine and E-5-(2-iodovinyl)-2'-deoxyuridine have such a selective antiviral activity against one type of virus (herpes simplex) and that their toxicity (in cell culture) is remarkably low.

Accordingly, the invention provides, in a first aspect, the new E-5-(2-halovinyl)-2'-deoxyuridines in particular E-5-(2-bromovinyl)-2'-deoxyuridine and E-5-(2-iodovinyl)-2'-deoxyuridine. In a second aspect, the invention provides a method of preparing E-5-(halovinyl)-2'-deoxyuridines which comprises reacting a hydroxyl-protected reactive 2-deoxy-D-erythro-pentofuranosyl derivative with a bis(trialkyl)silyl derivative of E-5-(2-halovinyl)-uracil and thereafter removing any trialkylsilyl groups and hydroxyl-protecting groups. In a third aspect, the invention provides a medicine for treatment of virus diseases caused by herpes simplex, which medicine contains an E-5-(2-halovinyl)-2'-deoxyuridine, in particular E-5-(2-bromovinyl)-2'-deoxyuridine or E-5-(2-iodovinyl)-2'-deoxyuridine, as an active ingredient. In a fourth aspect the invention provides a method of preparing such a medicine, which comprises combining an E-5-(2-halovinyl)-2'-deoxyuridine in particular E-5-(2-bromovinyl)-2'-deoxyuridine or E-5-(2-iodovinyl)-2'-deoxyuridine with a conventional excipient. Further, in a fifth aspect, the invention provides a bis(trialkyl)silyl derivative of E-5-(2-halovinyl)-uracil as a useful intermediate.

The method of chemical preparation of the invented compounds will now be described in more detail.

In its preferred form, this method involves a condensation reaction between a hydroxyl-protected reactive 2-deoxy-D-erythro-pentofuranosyl derivative of formula (II) and a bis(trialkyl)silyl derivative of E-5-(2-halovinyl)uracil represented by formula (III), followed by removal of any trialkylsilyl group and hydroxyl-protecting groups from the resulting molecule.

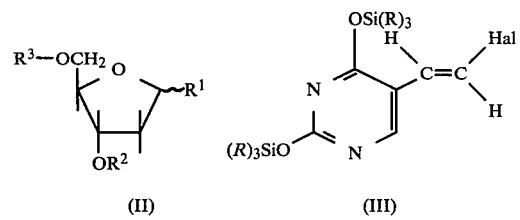

In these formulae, R is an alkyl group, preferably methyl; $R^1$ is a readily displaceable group, preferably either methoxy (in which case the compound II is a mixture of α and β-anomers) or chloro (in which case compound II is the α-anomer); $R^2$ and $R^3$ are hydroxyl-protecting groups, preferably p-toluoyl; and Hal is a bromine or iodine atom.

If $R^1$ is chloro, a Lewis acid catalyst may be used but is not necessary. If $R^1$ is methoxy, a Lewis acid catalyst is required. Suitable Lewis acid catalysts include molecular sieves, stannic and mercuric halides, viz. the chlorides and bromides, and trimethylsilyl perfluoroalkylsulphonates.

The quantity of the catalyst employed depends on the specific catalyst chosen. When mercuric halide is employed, best results are often obtained with small quantities, i.e. less than a tenth molar proportion, preferably a one-hundredth molar proportion.

The choice of solvent is not critical to the success of the reaction, though it is essential that this solvent be inert to the starting materials and products, and it is preferred that it dissolves both starting compounds (II) and (III) and where appropriate, the catalyst, in a sufficient degree. In order to ensure that the solvents are inert to compound (III), they should be rigorously dried. Examples of suitable solvents include acetonitrile, liquid aromatic hydrocarbons such as benzene and toluene, and halogenated alkanes such as dichloromethane, 1,2-dichloroethane and carbon tetrachloride.

The temperature at which the reaction is carried out is not critical, but as the sugar derivatives (II) decompose readily at elevated temperatures it is better to carry out the reaction at room temperature or below.

The reaction should be carried out in a dry atmosphere in order to prevent hydrolysis of the trialkylsilyl derivative by atmospheric moisture.

The time for which the reaction is allowed to proceed depends upon the particular catalyst and solvent employed. The course of the reaction can be followed by thin layer chromatography, and the reaction is allowed to continue until the maximum yield of product has been obtained. The reaction mixture is then worked up to give a crude product which is purified by crystallisation or chromatography.

The protecting groups may be removed by standard methods; for example, the trialkylsilyl groups and hydroxyl protecting groups are removed by hydrolysis or alcoholysis. The process of the invention usually produces a mixture of α and β-anomers in a proportion which depends to some extent upon the catalyst.

It is normally preferable to separate the β-anomer, i.e. the desired form of E-5-(2-halovinyl)-2'-deoxyuridine, from any mixture of anomers. These may be separated from the purified anomeric mixture and it is generally preferred to effect the separation before the hydroxyl protecting groups are removed.

The separation of the anomeric mixture may be effected by fractional crystallisation and/or by chromatography on silica gel. The precise solvent or solvent mixture which is used for this separation depends upon the specific hydroxyl-protected derivative (if hydroxyl-protecting groups are still present) and may e.g. be selected by prior small-scale experiments on thin-layer chromatographic plates. In these experiments, the anomers so separated may be characterised by NMR-spectroscopy.

Where $R^2$ and $R^3$ represent the preferred protecting groups, i.e. p-toluoyl, we have found that the best method for obtaining pure protected β-anomer is firstly to chromatograph the crude reaction product on silica gel eluting with benzene:ethyl acetate to obtain a purified anomeric mixture, and subsequently to crystallise from methanol. The pure protected β-anomer crystallises preferentially from this solution. This can subsequently be hydrolysed to give E-5-(2-halovinyl)-2'-deoxyuridine.

The starting materials of formula (II) have been described earlier and may be prepared from 2-deoxy-D-erythro-pentofuranose by methylation of the 1-hydroxyl group, incorporation of protecting groups to the hydroxyl groups at 3 and 5, and where required by replacement of the 1-methoxy group by chloro (compare e.g. C. C. Bath, in Synthetic Procedures in Nucleic Acid Chemistry, by Tipson R. S., and Zorbach W. W., eds, Interscience, Vol. 1 521–522 (1968).

The starting materials of formula (III) are novel and also form part of the invention. These compounds may be prepared by silylating E-5-(2-halovinyl)uracil with a silylating agent such as hexamethyldisilazane or trimethylchlorosilane or mixtures thereof. The E-5-(2-halovinyl)uracil may simply be obtained by brominating or iodinating 5-vinyluracil followed by the elimination of HBr or HI by the action of heat. (compare Bleackley et al, Tetrahedron, Vol. 32, 2795–2797 (1976).

The invented chemical synthesis as well as the physical constants of the end product and the preparation of the starting materials of formula (III) are illustrated further in the following examples, which should not be construed however, to restrict the invention.

EXAMPLE 1

Preparation of E-5-(2-bromovinyl)uracil 5-vinyluracil (2.75 g, 20 mmoles) was dissolved in dry dimethylformamide (250 ml). To this solution was added a solution of bromide (3.2 g, 20 mmoles) in dry dimethylformamide (30 ml). The reaction mixture was shaken until colourless and then heated at 100° for 1 hour. The solution was then evaporated under reduced pressure to a brown oil to which was added water (30 ml). The resulting pink suspension was filtered and the pale pink solid recrystallised from methanol to give E-5-(2-bromovinyl)uracil (3.62 g, 84% yield).

NMR: δ (d6DMSO): 11.2 (2-H,bd, N-H's), 7.7 (1-H, d, H-6, J=6 Hz) 7.3 (1-H, E-(trans)vinylic H-2', J=13 Hz), 6.8 ppm (1-H, E-(trans)vinylic H-1', J=13 Hz). UV: λmax 290 nm (ε, 9,930), 251 nm (ε, 17,500), λmin 275 nm (ε, 8,280) at pH-1, λmax 305 (ε, 11,400), 267 nm (ε, 15,400), λmin 290 nm (ε, 10,500) at pH-13.

Preparation of E-5-(2-bromovinyl)-3',5'-di-Q-p-toluoyl-2'-deoxyuridine and its α-anomer E-5-(2-bromovinyl)uracil (3.62 g, 16.7 mmoles) was suspended in hexamethyldisilazane (15 ml) and trimethylsilylchloride (0.1 ml) was added. The suspension was boiled under reflux for 1 h whereupon a clear solution was formed. The excess of solvent was removed under high vacuum and the residual oil distilled under high vacuum at 120°–130° in a Kugelrohr furnace. This gave this bistrimethylsilylated derivate as a colourless oil (5.04 g, 84% yield).

NMR: δ (CCl4): 8.05 (1-H,s,H-6), 6.83 (2-H,s,vinylic H's), 0.38, 0.30 ppm (18H,2s,Me3Si- on -2-O- and 4-O-) (Me4Si external standard).

The bistrimethylsilylated E-5-(2-bromovinyl)uracil (5,04 g, 14 mmoles) was dissolved in dry dichloroethane (50 ml) and added to a solution of 1-chloro-2-deoxy-3,5-di-O-p-toluoyl-α-D-erythro-pentofuranose (4,0 g, 12.6 mmoles) in dry dichloroethane (50 ml). The reaction mixture was magnetically stirred at 22° for 8 H and then evaporated to dryness under reduced pressure. The resulting oil was applied to a silica gel column and a crude separation was obtained using benzene-ethylacetate (7:3) as eluent, giving a total yield of the nucleosidic product of 5.3 g (88%). NMR spectroscopy indicated the ratio of anomers to be 1.3:1, ε:β. Further column chromatography in chloroform-propan-2-ol (99:1) gave more of the separated anomers. The farther running nucleoside was recrystallised from methanol to give the β-anomer as colourless crystals.

NMR: δ (CDCl3): 8.28 (1-H,s, N-H), 7.94 (4-H,d, aromatic H's), 7.41 (1-H,s, H-6), 7.26 (5-H, m, aromatic H's and E-vinylic H-2"), 6.40 (1-H, t, H-1'), 6.08 (1-H, d, E-vinylic H-1", J=13 Hz), 5.62 (1-H, d, H-3'), 4.72 (2-h, dd, H-5'), 4.54 (1-H, m, H-4'), 2.7 (2-H, bm, H-2'), 2.42 ppm (6-H, s, CH3's). UV: λmax 244 nm (ε, 37,400), 286 nm (sh) (ε, 8,550) in ethanol. M.pt. 186°–188° (dec.).

The α-anomer was recrystallised from methanol as white needles.

Preparation of E-5-(2-bromovinyl)-2'-deoxyuridine

E-5-(2-bromovinyl)-2'-deoxy-3',5'-di-O-p-toluoyluridine (0.924 g, 1,6 mmoles) was dissolved in a solution of sodium methoxide in methanol (15 ml, 0.1 M) and the mixture allowed to stand at 22° for 24 h. The solution was neutralised by careful addition of Dowex 50 (H+form) to pH 6 and then evaporated to a white solid. This was triturated with ether (3×10 ml), and dried under vacuum to give crude E-5-(2-bromovinyl)-2'-deoxyuridine (508 mg, 94% yield). This was recrystallised from methanol-water to give white needles M.Pt 123°–125° (d).

NMR: δ (d6DMSO): 11.24 (1=H,s,N-H), 8.08 (1-H,s,H-6), 7.24 (1-H,d, E-vinylic H-2"), 6.81 (1-H,d, E-vinylic H-1", J=13 Hz), 6.10 (1-H,t,H-1), 5.18 (1-H,d,OH-3'), 5.02 (1-H,t,OH-5'), 4.22 (1-H,m,H-3'), 3.78 (1-H,m,H-4'), 3.58 (2-H,m,H-5), 2.12 ppm (2-H,m,H-2'). UV: λmax 253 nm (ε, 13,100), 295 nm (ε, 10,300), λmin 274 nm (7,500) in ethanol.

The α-anomer could be deblocked in an analogous manner.

EXAMPLE 2

Preparation of E-5-(2-iodovinyl)uracil 5-vinyluracil (1.1 g, 8 mmoles) was dissolved in dry dimethylformamide (40 ml). To this solution was added a solution of iodine monochloride (1.28 g, 8 mmoles) in dry dimethylformamide (20 ml). The reaction mixture was allowed to stand, with occasional shaking, for 30 minutes and then heated at 100° for 30 minutes. The solution was then evaporated under reduced pressure to a brown oil to which was added water (20 ml). The resulting dark brown suspension was filtered and the brown solid collected and dried giving crude E-5-(2-iodovinyl)uracil (1.6 g, 76% yield). For the next stage this was not purified further.

NMR: δ (d6DMSO): 11.1 (2-H,bd,N-H's), 7.7 (1-H,d,H-6,J=6 Hz), 7.2 ppm (2-H's, vinylic H's) UV: λmax 294 nm (ε, 9,900), 250 nm (ε, 15,200), λmin 278 nm (ε, 9,250) at pH-1, λmax 310 nm (ε, 12,200), λmax 262 nm (ε, 15,850), λmin 290 nm (ε, 10,050) at pH-13.

Preparation of E-5-(2-iodovinyl)-3',5'-di-O-p-toluoyl-2'-deoxyuridine and its α-anomer E-5-(2-iodovinyl)uracil (1 g, 3.8 mmoles) was suspended in hexamethyldisilazane (8 ml) and trimethylsilylchloride (0.1 ml) was added. The suspension was boiled under reflux for 1 H, whereupon a clear solution was formed. The excess of solvent was removed under high vacuum and the residual oil distilled under high vacuum at 130°–160° in a Kugelrohr furnace. This gave the bistrimethylsilylated derivative as a yellow oil (554 mg, 36% yield).

NMR: δ (CCl4): 8.0 (1-H,s,H-6), 7.2 (1-H,d,E-(trans)-vinylic H-2',I=15 Hz), 6.8 (1-H,d,E-(trans)vinylic H-1',J=15 Hz), 0.4, 0.3 ppm (18-H, 2s, Mc3Si- on 2-O- and 4-O-).

The vinylic coupling constants of 15 Hz showed the configuration about the double bond to be E.

Condensation of the bistrimethylsilylated derivative with 1-chloro-2-deoxy-3,5-di-O-p-toluoyl-α-D-erythro-pento-furanose was carried out in an analogous manner to that previously described for the 5-(2-bromovinyl)-derivative. The α and β-anomers were separated by column chromatography in benzene-ethylacetate (8:2).

The farther running nucleoside was recrystallised from methanol to give the β-anomer as colourless crystals.

NMR: δ (CDCl3): 8.5 (1-H,bs,N-H), 6.45 ppm (2-H,m,H-1' and E-(trans)vinylic H-1"). UV: λmax 242 nm (ε, 33,950), λmax 295 nm (ε, 9,650), λmin 272 nm (ε, 7,850) in ethanol.

The α-anomer was recrystallised from methanol as white needles.

Preparation of E-5-(2-iodovinyl)-2'-deoxyuridine

E-5-(2-iodovinyl)-2'-deoxy-3',5'-di-O-p-toluoyl-uridine (84 mg, 0.14 mmoles) was dissolved in a solution of sodium methoxide in dry methanol (3 ml, 0.1 M) and the mixture allowed to stand at 22° for 5 H. The solution was neutralised by careful addition of Dowex 50 (H+form) to pH-6 and then evaporated to a yellow oil. This was co-evaporated with methanol to give a pale yellow solid of crude E-5-(2-iodovinyl)-2'-deoxyuridine (22 mg, 42% yield).

NMR: δ (d6DMSO): 11.6 (1-H,bs,N-H), 8.08 (1-H,s,H-6), 7.17 (2-H,s,vinylic H's), 6.14 ppm (1-H,H-1',J=6 Hz). UV: λmax 250 nm (ε, 14,100), λmax 295 nm (ε, 11,450), λmin 275 nm (ε, 8,450) in ethanol.

The α-anomer could be deblocked in an analogous manner.

Reference will now be made to a series of biological tests to show the specific antiviral and high antiviral index of the invented compound.

In these tests, the effect of E-5-(2-halovinyl)-2'-deoxyuridine and related compounds on the growth and yield of viruses in cell cultures was measured.

The compounds tested were: 2'-deoxy-5-vinyluridine (prepared according to Bobek et al: J. Org.Chem. 40,2377–2379 (1975); 5-(1-chlorovinyl)-2'-deoxyuridine (custom made); E-5-(2-bromovinyl)-2'-deoxyuridine (prepared in accordance with the foregoing example 1); E-5-(2-iodovinyl)-2'-deoxyuridine (prepared in accordance with the foregoing example 2); 2'-deoxy-5-ethynyluridine (prepared according to Perman et al: Tetrahedron Letters, 28, 2427–2430, (1976); and 2'-deoxy-5-iodouridine (provided by Ludeco, Brussels). All compounds were β-anomers, unless stated otherwise.

5-(1-chlorovinyl)-2'-deoxyuridine was prepared by the action of HCl on 2'-deoxy-5-ethynyluridine. The physical constants of this compound are: M.pt. 108–110 (d).

NMR: δ (d6DMSO): 11.2 (1-H,bs,N-H), 8.37 (1-H,s,H-6), 6.43 (1-H,s, vinylic H, trans to heterocyclic ring), 6.18 (1-H,t,H-1'), 5.54 (1-H,s, vinylic H, cis to heterocyclic ring), 5.1 (2-H,bs,O-H), 4.25 (1-H,m,H-3'), 3.86 (1-H,m,H-4'), 3.70 (2-H,m,H-5'), 2.17 ppm (2-H,m,H-2'). UV: λmax 234 nm (ε, 9,370), 282 nm (ε, 10,500), λmin 259 nm (ε, 6,550) at pH 6.

The compounds were tested on vaccinia and herpes simplex-1 (strain KOS) virus. These viruses were grown in primary rabbit kidney (PRK) and human skin fibroblast (HSF) cell cultures.

The technique for measuring virus growth in cell cultures has been described by De Clercq et al., Biochem. Pharmacol., 24, 523–527, (1975), which is incorporated herein by way of reference.

Test I

In this test, the inhibitory activity of E-5-(2-halovinyl)-2'-deoxyuridines and related compounds to vaccinia and herpes simplex-1 viruses in PRK and HSF cell cultures was measured. The cells were grown to confluency in either glass tubes (PRK) or plastic microplates (HSF). When confluent, the cells were inoculated with 100 CCID$_{50}$ of either vaccinia or herpes simplex-1 virus. One CCID$_{50}$ corresponds to the cell culture infecting dose-50, that is the virus dose required to infect 50% of the cell cultures. One hour after virus inoculation, the compounds were added at varying concentrations (ranging from 0.001 μg/ml to 100 μg/ml). For each virus-cell system, the ID$_{50}$ was determined. ID$_{50}$ corresponds to the inhibitory dose-50, that is the concentration of compound required to suppress the cytopathic effect to the virus by 50%. This cytopathic effect (CPE) was recorded as soon as it reached completion in the untreated virus-infected cell cultures (generally, 3 days after the cells has been inoculated with the virus). The results are given in Table I, where the data represent average values for three separate experiments.

TABLE I

Antiviral activity of E-5-(2-halovinyl)-2'-deoxyuridines and related 2'-deoxyuridine analogs in primary rabbit kidney (PRK) and human skin fibroblast (HSF) cell cultures.

| | ID$_{50}$ (μg/ml) | | | |
| --- | --- | --- | --- | --- |
| Compound | Vaccinia (PRK) | Vaccinia (HSF) | Herpes simplex-1 strain KOS (PRK) | Herpes simplex-1 strain KOS (HSF) |
| 2'-deoxy-5-vinyluridine | 0.4 | 0.1 | 0.04 | 0.07 |
| 5-(1-chlorovinyl)-2'-deoxyuridine | 0.4 | 0.7 | 0.4 | 2 |
| E-5-(2-bromovinyl)-2'-deoxyuridine | 7 | 0.7 | 0.007 | 0.007 |
| E-5-(2-iodovinyl)-2'-deoxyuridine | 10 | — | 0.01 | — |
| 2'-deoxy-5-ethynyluridine | 0.2 | 0.1 | 0.07 | 0.4 |
| 2'-deoxy-5-iodouridine | 0.2 | 0.2 | 0.2 | 0.7 |

Test 2

Further, the inhibitory effect of E-5-(2-bromovinyl)2'-deoxyuridine and related compounds on herpes simplex-1 virus multiplication in PRK cell cultures was measured.

Confluent PRK cell monolayers in plastic Petri dishes (diameter: 55 mm) were inoculated with herpes simplex-1 (4.5 log$_{10}$ PFU/0.5 ml/Petri dish) for 1 hour at 37° C. and, immediately thereafter, exposed to 0.1 μg/ml of either of the compounds to be tested. The cell cultures were then incubated for varying times (1,2 or 3 days) at 37° C. At the end of the incubation period the cells were frozen at −70°, and the cell homogenates were assayed for virus content by plaque formation in VERO cell cultures (VERO=a continuous cell line of green monkey cells). The results are presented in Table 2 as the differences in virus yield between the treated virus-infected cell cultures and the untreated virus-infected cell cultures. PFU means plaque formation units.

TABLE 2

Inhibitory effect of E-5-(2-bromovinyl)-2'-deoxyuridine and related 2'-deoxyuridine analogs on herpes simplex-1 (strain KOS) virus multiplication in primary rabbit kidney (PRK) cell cultures.

| | | Reduction of virus yield, as compared to control (untreated virus-infected) cell culture | | |
| --- | --- | --- | --- | --- |
| | Dose | Days after infection | | |
| Compound | (μg/ml) | 1 | 2 | 3 |
| 2'-deoxy-5-vinyluridine | 0.1 | 2.4 | 1.1 | 1.0 |
| 5-(1-chlorovinyl)-2'-deoxyuridine | 0.1 | 0.2 | 0.4 | 0.2 |
| E-5-(2-bromovinyl)-2'-deoxyuridine | 0.1 | 3.8 | 2.6 | 0.8 |
| 2'-deoxy-5-ethynyluridine | 0.1 | 0.2 | 0.2 | 0.1 |
| 2'-deoxy-5-iodouridine | 0.1 | 1.2 | 0.9 | 0.7 |

Test 3

The antimetabolic activity of E-5-(2-bromovinyl)-2'-deoxyuridine and related compounds in PRK cells cultures was measured.

(a) In a first experiment, the incorporation of certain radiolabelled DNA precursors into DNA of the cells, and the effect of 5-(2-bromovinyl)-2'-deoxyuridine and related compounds thereon, was tested. The technique has been described by De Clercq et al in Biochemical Pharmacology, 26, 794–797 (1977) and by De Clercq et al in Molecular Pharmacology, in press, 1978, which are incorporated herein by way of reference.

The DNA precursors as used were (methyl-$^3$H) (2'-deoxythymidine) (TdR), and (2-$^{14}$C) (2'-deoxyuridine) (UdR).

The cells were exposed to 0.12 μCi:0.01 nmol (methyl-$^3$H)TdR (per 10$^5$ cells) or 14 μCi/250 nmol (2-$^{14}$C)UdR (per 10$^5$ cells) for 16 hours in the presence of varying concentrations of the compounds (ranging from 1 to 100 μg/ml). Incorporation of the radiolabelled precursor was then measured as described and the ID$_{50}$ was determined. ID$_{50}$ corresponds to the inhibitory dose-50, that is the concentration of compound required to inhibit incorporation of either (methyl-$^3$H)TdR or (2-$^{14}$C)UdR by 50%. The results are given in Table 3.

(b) In a second experiment, the total cell number after exposure to E-5-(2-bromovinyl)-2'-deoxyuridine and related compounds was measured. The cells were plated onto plastic Petri dishes (diameter: 55 mm) at approximately 800.000 cells/petri dish in the presence of varying concentrations of the compounds (ranging from 0.01 to 100 μg/ml). After a 3-day incubation period at 37° (in the presence of 5% CO$_2$), the cell culture medium was removed, the cells were brought into suspension with trypsin and counted with a coulter counter model ZB. The results are given in Table 3. ID$_{50}$ corresponds to the inhibitory dose-50, that is the concentration of compound required to reduce the total cell number by 50%.

TABLE 3

Antimetabolic activity of E-5-(2-bromovinyl)-2'-deoxyuridine and related 2'-deoxyuridine analogs in primary rabbit kidney (PRK) cell cultures.

| Compound | ID$_{50}$ (µg/ml) | | |
|---|---|---|---|
| | (methyl-$^3$H)TdR incorporation into DNA | (2-$^{14}$)UdR incorpor. into DNA | Total cell number |
| 2'-deoxy-5-vinyluridine | 20 | 8 | 8 |
| 5-(1-chlorovinyl)-2'-deoxyuridine | 27 | <6 | 2 |
| E-5-(2-bromovinyl)-2'-deoxyuridine | 70 | 35 | >33 |
| 2'deoxy-5-ethynyluridine | 100 | <<6 | 0.3 |
| 2'-deoxy-5-iodouridine | 2.5 | 1.2 | 6 |

Test 4

Finally, the antiviral index of 5-(2-bromovinyl)-2'-deoxyuridine and its related compounds in PRK cell cultures was determined as a result of the measurements made in the foregoing tests.

The antiviral index was calculated by dividing the "antimetabolic" ID$_{50}$ by the "antiviral" ID$_{50}$. The "antimetabolic" ID$_{50}$ corresponded to the dose required to reduce the cell number by 50% whereas the "antiviral" ID$_{50}$ corresponded to the dose required to inhibit the cytopathic effect of herpes simplex-1 by 50%. The results are given in Table 4.

TABLE 4

Antiviral index of E-5-(2-bromovinyl)-2'-deoxyuridine and related 2'-deoxyuridine analogs in primary rabbit kidney (PRK) cell cultures.

| Compound | Antiviral index |
|---|---|
| 2'-deoxy-5-vinyluridine | 200 |
| 5-(1-chlorovinyl)-2'-deoxyuridine | 5 |
| E-5-(2-bromovinyl)-2'-deoxyuridine | >5000 |
| 2'-deoxy-5-ethynyluridine | 5 |
| 2'-deoxy-5-iodouridine | 30 |

It will be noted from the foregoing test results that E-5-(2-bromovinyl)-2'-deoxyuridine, and E-5-(2-iodovinyl)-2'-deoxyuridine unlike their related compounds, have a specific antiviral activity and at least as far as E-5-(2-bromovinyl)-2'-deoxyuridine is concerned) a remarkably high antiviral index against herpes simplex virus. Thus, they may be used with advantage for treatment of diseases caused by this virus in man and animal.

Pharmaceutical compositions comprising E-5-(2-bromovinyl)-2'-deoxyuridine or E-5-(2-iodovinyl)-2'-deoxyuridine as an active ingredient may have the form of powders, suspensions, solutions, emulsions as well as ointments and pastes, and may be used for parenteral (intravenous, intradermal, intramuscular, intrathecal, . . . ) injections, oral, rectal, intravaginal and intranasal administration or topical application (e.g. to lesions of skin, mucosa and eye). These compositions may be prepared by combining the active ingredient(s) with pharmaceutically acceptable excipients which are normally used for this purpose. These excipients may comprise aqueous or non-aqueous solvents, stabilisers, suspenders, dispersers, wetting agents and the like and will be known to those skilled in the pharmaceutical art. Further, the composition may comprise any suitable additives like polyethyleneglycols, and, if necessary, dyestuffs, perfumes and the like.

The pharmaceutical compositions will contain at least 0.1% by weight/volume of the active ingredient. The actual concentration will depend on the disease and on the chosen route of administration. In general, this concentration will be between 0.1% and 100%.

What we claim is:

1. E-5(2-halogenovinyl)-2'-deoxyuridines of the formula:

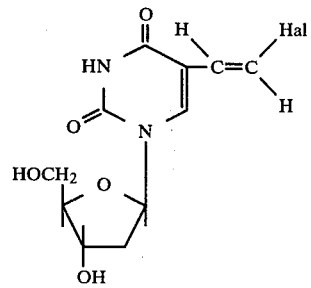

wherein Hal represents a halogen atom selected from the group consisting of bromine and iodine.

2. An E-5-(2-halogenvinyl)-2'-deoxyuridine as in claim 1, wherein Hal represents bromine.

3. An E-5-(2-halogenovinyl)-2'-deoxyuridine as in claim 1, wherein Hal represents iodine.

4. A pharmaceutical composition for the treatment of herpes simplex infections comprising as an active ingredient an antiviral effective amount of an E-5-(2-halogenovinyl)-2'-deoxyuridine compound of the formula:

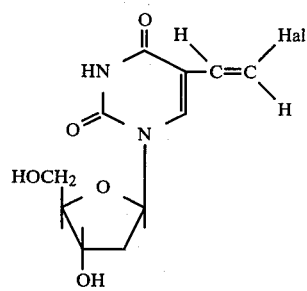

wherein Hal represents a halogen atom selected from the group consisting of bromine and iodine, and a pharmaceutically acceptable carrier, diluent or excipient.

5. A pharmaceutical composition as in claim 4, wherein Hal represents bromine.

6. A pharmaceutical composition as in claim 4, wherein Hal represents iodine.

7. A method for treating herpes simplex infections comprising administering an effective antiviral amount of an E-5-(2-halogenovinyl)-2'-deoxyuridine compound of the formula:

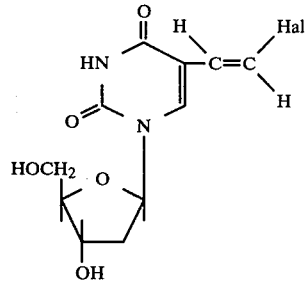

wherein Hal represents a halogen atom selected from the group consisting of bromine and iodine.

8. The method for treating herpes simplex infections according to claim 7, wherein Hal represents bromine.

9. The method for treating herpes simplex infections according to claim 7, wherein Hal represents iodine.

UNITED STATES PATENT AND TRADEMARK OFFICE
CERTIFICATE OF CORRECTION

PATENT NO. : 4,424,211

DATED : January 3, 1984

INVENTOR(S) : Jones et al

It is certified that error appears in the above-identified patent and that said Letters Patent are hereby corrected as shown below:

In the Heading of the Patent, after the category "Related U.S. Application Data" insert --[30] Foreign Application Priority Data Apr. 24, 1978 [GB] Great Britain.................. 16159--.

*Signed and Sealed this*

*Seventh* Day of *August 1984*

[SEAL]

*Attest:*

GERALD J. MOSSINGHOFF

*Attesting Officer*     *Commissioner of Patents and Trademarks*